US009961589B2

(12) United States Patent
Wang (10) Patent No.: US 9,961,589 B2
(45) Date of Patent: May 1, 2018

(54) MULTI-CHANNEL COMMUNICATION SCHEME FOR MEDICAL BODY AREA NETWORK (MBAN) TO MEET DUTY CYCLE REGULATION (71) Applicant: KONINKLIJKE PHILIPS N.V., Eindhoven (NL)

(72) Inventor: Dong Wang, Scarsdale, NY (US)

(73) Assignee: Koninklijke Philips N.V., Eindhoven (NL)

(*) Notice: Subject to any disclaimer, the term of this patent is extended or adjusted under 35 U.S.C. 154(b) by 0 days. days.

(21) Appl. No.: 15/128,130

(22) PCT Filed: Mar. 9, 2015

(86) PCT No.: PCT/IB2015/051696
§ 371 (c)(1),
(2) Date: Sep. 22, 2016

(87) PCT Pub. No.: WO2015/145283
PCT Pub. Date: Oct. 1, 2015

(65) Prior Publication Data
US 2017/0111824 A1 Apr. 20, 2017

Related U.S. Application Data (60) Provisional application No. 61/969,886, filed on Mar. 25, 2014.

(51) Int. Cl.
H04W 72/10 (2009.01)
H04W 28/08 (2009.01)
A61B 5/00 (2006.01)
H04B 13/00 (2006.01)
H04L 29/08 (2006.01)

(52) U.S. Cl.
CPC ......... H04W 28/085 (2013.01); A61B 5/0024 (2013.01); H04B 13/005 (2013.01); H04L 67/125 (2013.01)

(58) Field of Classification Search
CPC ... H04W 28/085; H04W 72/04; H04W 72/12; H04B 13/005; H04L 67/125; A61B 5/0024; A61B 13/005
USPC .......... 128/903; 455/41.2, 452.1, 452.2, 447, 455/454; 600/300, 301; 370/252, 329, 370/328, 225, 242, 248, 332, 437
See application file for complete search history.

(56) References Cited

U.S. PATENT DOCUMENTS 4,827,943 A 5/1989 Bomn
4,958,645 A 9/1990 Cadell
(Continued)

FOREIGN PATENT DOCUMENTS

WO 2013035058 3/2013

Primary Examiner — Kamran Afshar
Assistant Examiner — Farid Seyedvosoghi (57) ABSTRACT A system (52) and a method maintain a medical body area network (MBAN) (62). Devices (56, 58) of the MBAN (62) are communicated (152) with over one or more channels of the MBAN (62). The one or more channels include a primary channel, and each of the devices (56, 58) is assigned to one of the one or more channels. Further, a duty cycle of each of the one or more channels is continuously monitored (156). In response to the duty cycle of the primary channel meeting or exceeding a duty cycle limit, a device (56, 58) of the devices (56, 58) is moved (158) to a secondary channel.

12 Claims, 6 Drawing Sheets (56) References Cited

U.S. PATENT DOCUMENTS

| | | | | |
|---|---|---|---|---|
| 2006/0050730 A1* | 3/2006 | Shvodian | .............. | H04W 74/02 |
| | | | | 370/458 |
| 2011/0149759 A1 | 6/2011 | Jollota | | |
| 2012/0172075 A1* | 7/2012 | Hyon | .................... | A61B 5/0015 |
| | | | | 455/501 |
| 2013/0023214 A1* | 1/2013 | Wang | .................... | A61B 5/0002 |
| | | | | 455/41.2 |
| 2013/0237777 A1* | 9/2013 | Patel | .................... | A61B 5/0024 |
| | | | | 600/301 |
| 2013/0245387 A1 | 9/2013 | Patel | | |
| 2013/0337749 A1* | 12/2013 | Wang | .................... | H04W 72/10 |
| | | | | 455/41.2 |

\* cited by examiner

MULTI-CHANNEL COMMUNICATION SCHEME FOR MEDICAL BODY AREA NETWORK (MBAN) TO MEET DUTY CYCLE REGULATION

CROSS REFERENCE TO RELATED APPLICATIONS

This application is the U.S. National Phase application under 35 U.S.C. § 371 of International Application No. PCT/IB2015/051696, filed Mar. 9, 2015, published as WO 2015/145283 on Oct. 1, 2015, which claims the benefit of U.S. Provisional Patent Application No. 61/969,886 filed Mar. 25, 2014. These applications are hereby incorporated by reference herein.

The present application relates generally to wireless communication. It finds particular application in conjunction with medical body area networks (MBANs), and will be described with particular reference thereto. However, it is to be understood that it also finds application in other usage scenarios and is not necessarily limited to the aforementioned application.

There is a general trend in the healthcare industry towards ubiquitous patient monitoring. Ubiquitous patient monitoring provides continuous and patient centric monitoring services during the whole care cycle and can significantly improve quality of care. For example, patient deterioration could be detected at an early stage and early intervention can effectively prevent severe adverse events. MBANs are one of the key enabling technologies for ubiquitous monitoring services. An MBAN replaces the tangle of cables tethering patients to their bedside monitoring units with wireless connections. An MBAN is a low-power wireless network of sensors around and/or on a patient used for monitoring a patient's physiological parameters.

Figure 1:
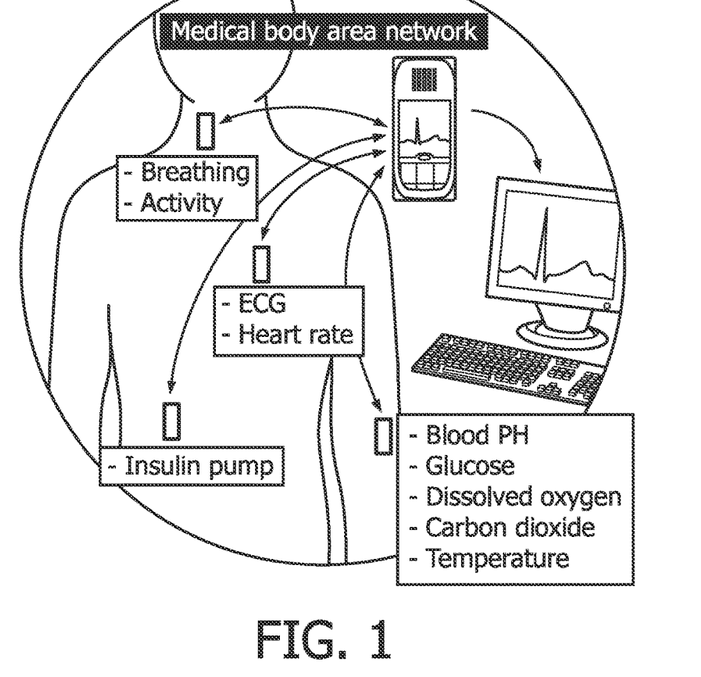
FIG. 1 illustrates a medical body area network (MBAN).

With reference to FIG. 1, a typical MBAN system includes several tiny sensor devices placed around and/or on a patient's body to capture physiological data of the patient, such as heart rate and electriocardiogram (ECG) signals. The captured data is forwarded to a hub device through a short-range and low-power MBAN. The hub device could be a local bedside monitoring device, a cell phone, a set-top-box, or other wireless device and usually has a connection to a backhaul communication network (e.g., a cellular network, such as a third generation (3G) or fourth generation (4G) cellular network, a local area network (LAN), etc.). The backhaul communication network is used to transfer the collected data to a remote patient monitoring system. The remote patient monitoring system is responsible for analyzing patients' physiological data and provides one or more of monitoring, diagnosing and treating services in real time.

MBANs provide a low-cost solution to extend patient monitoring services to areas that are currently not monitored (e.g., general wards, patient homes, etc.) and allow patients to walk around without discontinuing monitoring services. This makes it possible to discharge patients earlier from intensive care units (ICUs) or even hospitals, while still providing high quality care monitoring services. This can reduce healthcare costs significantly.

To facilitate MBAN deployment, the United States Federal Communications Commission (FCC) has recently allocated a dedicated MBAN band ranging from 2360 megahertz (MHz) to 2400 MHz for MBAN services. In Europe, the European Conference of Postal and Telecommunications Administrations (CEPT) and the Electronic Communications Committee (ECC) are considering allocating a dedicated MBAN band ranging from 2483.5 MHz to 2500 MHz for MBAN services. The MBAN bands are cleaner than the 2.4 gigahertz (GHz) industrial, scientific and medical (ISM) band, which is currently used by most wireless patient monitoring devices. Hence, the MBAN bands are useful for enhancing link robustness and providing medical-grade quality-of-service (QoS) in MBANs. Moreover, the MBAN bands are adjacent to the 2.4 GHz ISM band, which makes it possible to reuse low-cost, mature 2.4 GHz ISM band radios for MBAN services. Such radios include radios designed form the Institute of Electrical and Electronics Engineers (IEEE) 802.15.4 standard.

A challenge with the MBAN bands is that the allocations are not exclusive. Hence, MBAN services have to share the MBAN bands with other in-band users in many cases. Further, the allocations in some regions, such as Europe, include restrictions on the maximum duty cycle of MBAN operations to achieve harmonized coexistence. For example, the proposed MBAN regulation rules in Europe require that the duty cycle of an MBAN operating in a hospital be no larger than 10%. Such duty cycle limits also exist for other applications, such as implanted devices operating in the medical implant communication service (MICS) and the low power-active medical implant (LP-AMI) bands.

As the required data rate for MBAN services grows, duty cycle limits could become an issue for some MBAN service. Such limits may restrict the use of MBAN band for high-data rate MBAN services. For example, a 12-lead real-time ECG monitoring service may require an application layer data rate of 96 kilobits per second (Kbps), assuming a 500 hertz (Hz) sampling rate with 16 bit precision. With IEEE 802.15.4 radios having 250 kilobit per second (Kbps) physical layer (PHY) data rates, it is impossible to meet a 10% duty cycle limit. Further, even for other radios with higher physical layer data rates (e.g., IEEE 802.15.6 radios having approximately 1 megabit per second (Mbps) PHY data rates), it is still challenging to meet such a limit due to the communication protocol overhead (i.e., the overhead of the PHY, media access control (MAC), and application layers).

The present application provides a new and improved system and method which overcome the above-referenced problems and others.

In accordance with one aspect, a system for maintaining a medical body area network (MBAN) is provided. The system includes at least one controller configured to communicate with devices of the MBAN over one or more channels of the MBAN. The one or more channels include a primary channel, and each of the devices is assigned to one of the one or more channels. The at least one processor is further configured to continuously monitor a duty cycle of each of the one or more channels, and in response to the duty cycle of the primary channel meeting or exceeding a duty cycle limit, move a device of the devices to a secondary channel.

In accordance with another aspect, a method for maintaining a MBAN is provided. The method includes communicating with devices of the MBAN over one or more channels of the MBAN. The one or more channels include a primary channel, and each of the devices is assigned to one of the one or more channels. The method further includes continuously monitoring a duty cycle of each of the one or more channels, and in response to the duty cycle of the primary channel meeting or exceeding a duty cycle limit, moving a device of the devices to a secondary channel.

In accordance with another aspect, a coordinator device in a system for maintaining a network is provided. The coordinator device is configured to communicate with devices of the network over one or more channels of the network. The one or more channels include a primary channel, and each of the devices is assigned to one of the one or more channels. The coordinator device is further configured to continuously monitor a duty cycle of each of the one or more channels, and in response to the duty cycle of the primary channel exceeding a duty cycle limit, move a device of the devices to a secondary channel.

One advantage resides in compliance with duty cycle limits.

Another advantage resides in high data rate MBANs operating within duty cycle limits.

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

A solution to meet a duty cycle limit imposed upon a medical body area network (MBAN) is to do data compression on source data at sensor devices of the MBAN to reduce the amount of data to be transmitted. However, the solution has some disadvantages. The method puts extra requirements on computation and storage capabilities of the sensor devices, which may then increase the cost of the sensor devices. Further, the solution may affect battery lives of the sensor devices, which are dependent on the compression algorithm. Even more, a simple lossless compression algorithm may not be able to achieve sufficiently high compression ratios to meet the duty cycle limit. Moreover, the compression algorithm may increase the latency of medical data transmission, which may not be acceptable for latency sensitive services.

Nowadays, most of radio frequency (RF) radios can work on a wide frequency range that may cover several frequency bands. For example, Institute of Electrical and Electronics Engineers (IEEE) 802.15.4 and future IEEE 802.15.6 radios typically work in roughly the 2300-2500 megahertz (MHz) frequency range, which covers the United States MBAN band (i.e., 2360-2400 MHz), the 2.4 gigahertz (GHz) industrial, scientific and medical (ISM) band (i.e., 2400-2483.5 MHz), and the proposed Europe MBAN band (i.e., 2483.5-2400 MHz). The 2.4 GHz ISM band is always available for MBAN operations even if it is "dirty" (i.e., more likely to have interference) compared to the MBAN bands. Hence, the 2.4 GHz ISM band opens door to operate MBANs in different bands simultaneously to offload some traffic from a channel in the MBAN bands to other channel(s) outside the MBAN bands so that the duty cycle limit can be met.

According to the present application, a multi-channel communication scheme is provided to enable high data rate medical services in a dedicated MBAN band with a duty cycle limit. At least one channel in the MBAN band and at least one channel outside the MBAN band are used by an MBAN for communications. A hub device of the MBAN operates on all the channels while a sensor device may operate only on one channel. When a sensor device establishes a connection with the hub device, it provides data regarding its application and requirements (e.g., data rate, priority, etc.). Based on the provided data, the hub device assigns channels and/or schedules to the sensor device to ensure compliance with duty cycle limits. During operation, the hub device may adjust the channel and/or schedule allocations of its sensor devices to adapt to changes in the MBAN and to optimize the battery life of devices of the MBAN.

Figure 2:
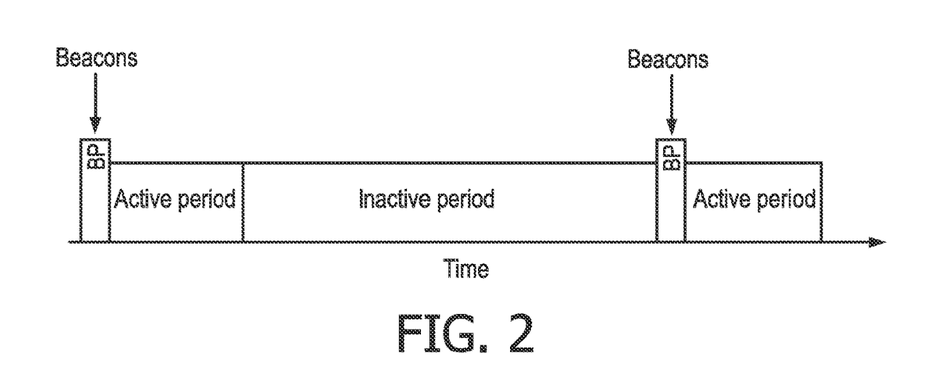
FIG. 2 illustrates a beacon based superframe structure.
Figure 3:
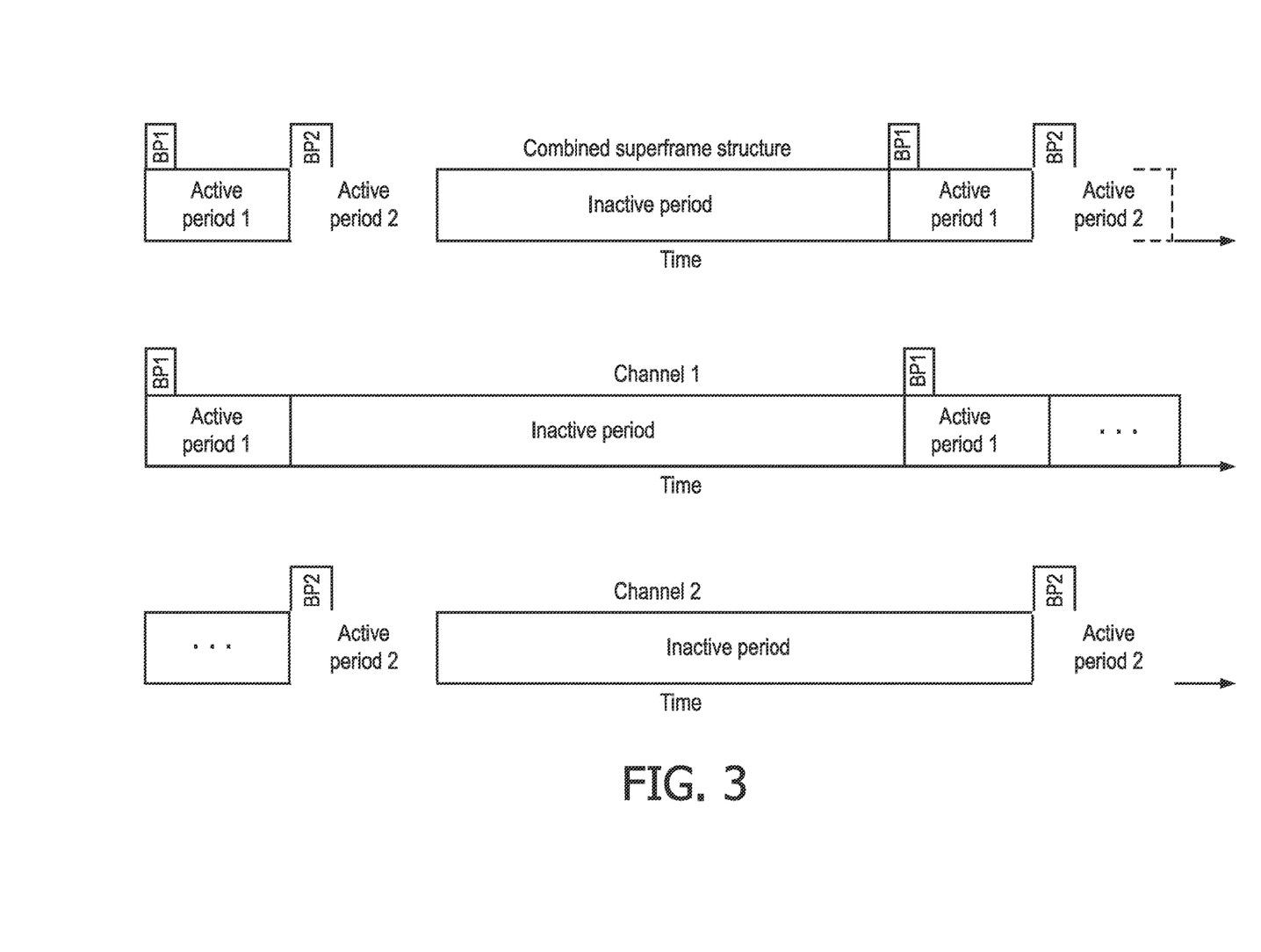
FIG. 3 illustrates beacon based superframe structures of first and second channels, as well as the combined superframe structure, of a multi-channel communications scheme.
Figure 4:
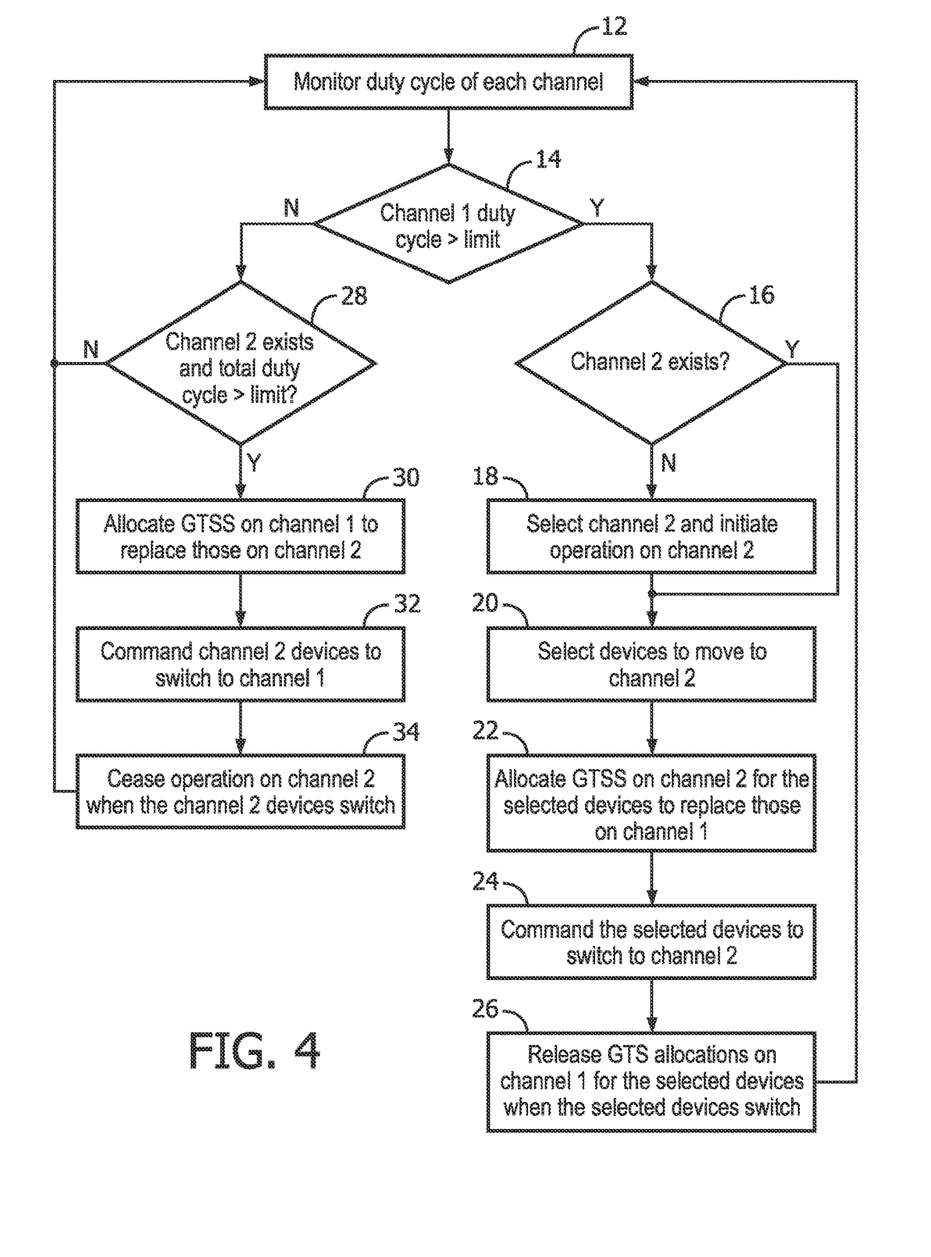
FIG. 4 illustrates beacon based superframe structures of K>2 channels, as well as the combined superframe structure, of a multi-channel communications scheme.

With reference to FIG. 2-4, the multi-channel communication scheme is described in greater detail. For ease of discussion, the description is made in the context of IEEE 802.15.4 radios. However, the multi-channel communication scheme has use with other types of radios, such as IEEE 802.15.6 radios. Also, for ease of discussion, the description is limited to only two channels. However, the multi-channel communication scheme can be extended to more than two channels.

With specific reference to FIG. 2, when an MBAN is initiated to operate in an MBAN band that has a duty cycle limit, a hub device of the MBAN picks a channel in the MBAN band (hereafter "the primary channel") and starts beacon transmissions to establish a beacon based superframe structure on the primary channel. As shown, the superframe structure includes a beacon, followed by active and inactive periods. Most popular MBAN wireless solutions, such as IEEE 802.15.6 and IEEE 802.15.4, support beacon based superframe structures. For example, IEEE 802.15.4 allows the use of a superframe structure with contention access period and contention free period.

Once the hub device starts beacon transmissions, the hub device can process sensor device association requests on the primary channel to establish MBAN communications between the hub and sensor devices, as described in the IEEE 802.15.4 protocol. In beacons of the primary channel, the hub device includes a minimum allowed priority level, which defines the minimum priority level that an MBAN device must have for it to associate with the hub device on the primary channel. Each sensor device has a pre-assigned priority level, based on the importance of the data it measures. If the hub device only operates on one channel, the priority level of primary channel is set to "0" to allow all the sensor devices to initiate device association procedures.

If an MBAN sensor device is configured to join an MBAN, it first scans the MBAN channels to locate beacons of the primary channel. Once it receives a beacon from the primary channel, it compares the minimum allowed priority level in the beacon with its priority level to determine whether it is allowed to associate with the MBAN on the primary channel. If its priority level is lower than the minimum allowed priority level of the beacon, the sensor device does not associate with the MBAN on the primary channel. Instead, it scans channels in a secondary band, such as the ISM band, to see if the MBAN has a secondary channel. If no secondary channel is found, the sensor device reports an association error.

In addition to processing association requests, the hub device continuously monitors the duty cycle of its MBAN on the primary channel. For example, the hub device can monitor the transmission times (i.e., duty cycles) in the contention access period and the contention free period. The contention access period is the period in which MBAN devices use a random access mechanism, such as carrier sense multiple access with collision avoidance (CSMA/CA), to obtain channel access. The contention free period is the period in which MBAN devices use guaranteed time slots (GTS) allocated by the hub device. The contention access period is usually for aperiodic event-driven data transfer, and the contention free period is usually for periodic vital sign measurements.

With the continuously monitored duty cycle, the hub device can evaluate whether its MBAN can meet the duty cycle limit. If the hub device determines that its MBAN exceeds the duty cycle limit (e.g., due to a burst data transfer triggered by an unexpected medical event), it selects a secondary channel in a secondary band, such as the 2.4 GHz ISM band, and starts beacon transmissions to establish a beacon based superframe structure on the secondary channel. As shown in FIG. 3, the active periods of the primary and secondary channels (illustrated as channels 1 and 2, respectively) are controlled so they do not overlap with each other. This allows the hub device to work on the two channels in a similar manner as time division multiple access (TDMA).

With reference to FIG. 3, the two superframes of the primary and secondary channels have the same period but can have different structures in terms of the length of contention access period and the length of contention free period. The primary channel in the MBAN band is reserved for "important" data transmission and can be accessed only by high priority MBAN devices. The secondary channel typically in the ISM band is used for all other communications and can be accessed by all devices of the MBAN. The two superframes belong to the same MBAN and share the same network identifier (ID) and device short addresses. Once a MBAN device is associated with the MBAN, it can operate on both channels if allowed by the hub device. This is to be contrasted with two separate MBANs operating in two separate channels independent of each other.

In the beacons transmitted on the primary channel (i.e., in the MBAN band), data about the superframe structure of the secondary channel is transmitted. The beacons are abbreviated as "BP" (for beacon packet) in FIG. 3. The data regarding the secondary channel can include location data identifying where the secondary channel is (e.g., central frequency or channel number) and timing data identifying the timing of the superframe structure of the secondary channel (e.g., the timing offset of the next superframe beacon transmission on the secondary channel relative to the start of the current beacon transmission on the primary channel, contention access period and contention free period structure data, etc.). The data regarding the secondary channel aids MBAN sensor devices assigned to the primary channel (i.e., sensor devices with priority levels exceeding the minimum allowed priority level of the primary channel) in communicating on the secondary channel. The beacons transmitted on the primary channel also include superframe structure data and other relevant data (e.g., GTS allocations, pending addresses, etc.) for only those MBAN devices that are assigned to the primary channel.

Devices that are assigned to the primary channel are allowed to access the secondary channel (i.e., the channel typically in the ISM band). For example, a device assigned to the primary channel can do contention based channel access in the contention access period of the secondary channel. Once the hub device begins operation on the secondary channel, it may change the minimum allowed priority level of the primary channel to prevent low priority unconnected MBAN devices from associating on the primary channel.

The beacons transmitted on the secondary channel have the same structure as the beacons defined by IEEE 802.15.4. Further, the beacons transmitted on the secondary channel include superframe structure data and other relevant data (e.g., GTS allocations, pending addresses, etc.) for only MBAN devices that are assigned to the secondary channel (i.e., devices with priority levels less than the minimum allowed priority level of the primary channel). Devices that are assigned to the secondary channel (i.e., the channel in the ISM band) are NOT allowed to access the primary channel (i.e., the channel in the MBAN band). This guarantees the duty cycle of the primary channel is manageable.

In the case that the hub device determines that it's MBAN operations on the primary channel will exceed the duty cycle limit, it shifts some communications from the primary channel in the MBAN band to the secondary channel, typically in the ISM band, so that the duty cycle of the primary channel is reduced and meets the duty cycle limit. In that regard, the hub device selects one or multiple MBAN devices that are currently assigned to the primary channel and moves these devices to the secondary channel. The selection criteria are designed so as to one or more of: 1) keep high priority devices on the primary channel as much as possible to maintain quality of service since channels in the MBAN band are typically cleaner than channels in the ISM band; and 2) allow as many sensor devices as possible operate on only one channel so that channel switch operations are minimized to save sensor device power.

Once the devices to be moved are selected, the hub device allocates GTS time slots on the secondary channel for the selected devices that have GTS allocations on the primary channel. The new GTS allocation data is then transmitted in the beacons of the secondary channel. Further, the hub device notifies the selected devices with a channel switch command that includes the addresses of the selected devices (or a series of channel realignment commands) and releases the GTS allocations of the selected devices on the primary channel once it is confirmed that all the selected devices switch to the secondary channel or a predefined waiting time period is expired.

When a sensor device on the primary channel receives a channel switch command from its hub device, it switches to the secondary channel and uses the data of the secondary channel that it receives from the beacons of the primary channel to assist with timing synchronization on the secondary channel. On the secondary channel, the moved device doesn't need to perform re-association. It receives beacons of the secondary channel to get necessary data (e.g., its new GTS allocation, if any) and then resumes its communications on the secondary channel. If the channel switch operation fails, the moved device becomes an orphan device and performs re-association. For those moved devices, the assigned channel becomes the secondary channel. Hence, the moved devices can only access the secondary channel and cannot go back to the primary channel. In contrast, devices assigned to the primary channel can obtain data regarding the secondary channel from the beacons of the primary channel and are allowed to access the secondary channel (e.g., do contention based channel access in the contention access period on the secondary channel).

When a hub device operates on two channels, a new sensor device can associate on either channel if that is allowed by the hub device. If such association is accepted by the hub device, the hub device picks a channel as the assigned channel and may send a channel switch command to request that the newly associated device switches to its assigned channel if the assigned channel is not the current channel. In this way, every device has an assigned channel.

In the case that a hub device operates on two channels, the hub device may decide to switch back to single-channel operation if it detects that the total duty cycle of its MBAN (i.e., the sum of the duty cycles of both the primary and secondary channels) falls below the duty cycle limit. If so, the hub device allocates GTS time slots on the primary channel to replace the GTS allocations on the secondary channel. The new GTS allocation data is then transmitted in the beacons of the primary channel and data about the secondary channel is removed from the beacons of the primary channel. Further, the hub device notifies the devices on the secondary channel with a channel switch command. In this channel switch command, the beacon timing data can be included to help the devices of the secondary channel acquire synchronization on the primary channel.

When a device on the secondary channel receives a channel switch command from its hub device, it switches to the primary channel. On the primary channel, the moved device doesn't need to perform re-association. It receives beacons of the primary channel to get necessary data (e.g., its new GTS allocation) and resumes its communications on the primary channel. If the channel switch operation fails, the device becomes an orphan device and performs re-association. After all the devices of the secondary channel switch to the primary channel or a predefined waiting time period expires, the hub device ceases operation on the secondary channel and only operates on the primary channel. Also, the hub device may reset the minimum allow priority level to "0".

To summarize, an MBAN can operate multiple channels simultaneously in a manner similar to TDMA. The channels may locate on multiple frequency bands: an MBAN band (e.g., 2360-2400 MHz), typically with a regulatory duty cycle limit, and a secondary band (e.g., the 2.4 GHz ISM band) without a duty cycle limit. The hub device has a primary channel in the MBAN band and may have a secondary channel in the secondary band.

The MBAN hub device is responsible for establishment of the MBAN. It maintains a beacon based superframe structure on each of its operating channels to facilitate MBAN sensor device medium access. The active periods of all the channels are timed so they do not overlap with each other to allow the hub device to operate on these channels in a manner similar to TDMA. To establish an MBAN, the hub device selects a primary channel in the MBAN band and starts beacon transmission on the primary channel. In the beacons of the primary channel, a minimum allow priority level P is transmitted. Each sensor device has a pre-assigned priority level and an unconnected sensor device joining the MBAN checks the minimum allow priority level received in the beacon to decide whether it has a high enough priority to associate with the MBAN on the primary channel. When the hub operates only a single channel, the minimum allow priority level may be set to "0" to allow MBAN sensor devices with any priority level to associate with the MBAN on the primary channel.

With reference to FIG. 4, the hub device continuously monitors 12 the duty cycle of the primary channel (illustrated as channel 1) to determine 14 if the duty cycle exceeds the duty cycle limit. If it determines 14 that the duty cycle exceeds the duty cycle limit, the hub device determines 16 whether a secondary channel (illustrated as channel 2) outside the MBAN band exists. If not, the hub device selects 18 a secondary channel outside the MBAN band and initiates 18 operation on the secondary channel. In initiating operation on the secondary channel, the hub device broadcasts data regarding the secondary channel in the beacons of the primary channel. The devices assigned to primary channel can use such data to access the secondary channel, but devices assigned to the secondary cannot access the primary channel.

If the secondary channel exists, or once the secondary channel is initiated, the hub device selects 20 devices on the primary channel to move to the secondary channel to offload some traffic from the primary channel to the secondary channel. The hub device selects the devices based on corresponding priorities and schedules. After selecting 20 the devices, GTSs are allocated 22 on the secondary channel for the selected devices to replace corresponding GTS allocations on the primary channel. Further, the selected devices are commanded 24 to switch to the secondary channel. Once the selected devices complete the switch, the corresponding GTS allocations are released 26 on the primary channel and the hub device resumes monitoring 12 of the duty cycle of the primary channel.

If the duty cycle of the primary channel does not exceed the duty cycle limit, a determination 28 is made as to whether a secondary channel exists and whether the total duty cycle (i.e., the sum of the duty cycles of the primary and secondary channels) is less than the duty cycle limit. If not, the hub device continues monitoring 12 the duty cycle of the primary channel. If so, the hub device allocates 30 GTSs on the primary channel to replace those on the secondary channel. Further, the devices of the secondary channel are commanded 32 to switch to the primary channel. Once the devices of secondary channel complete the switch, operation on the secondary channel ceases 34 and the hub device continues monitoring 12 the duty cycle of the primary channel. The cessation includes removing data about the secondary channel is in the beacons of the primary channel.

Figure 5:
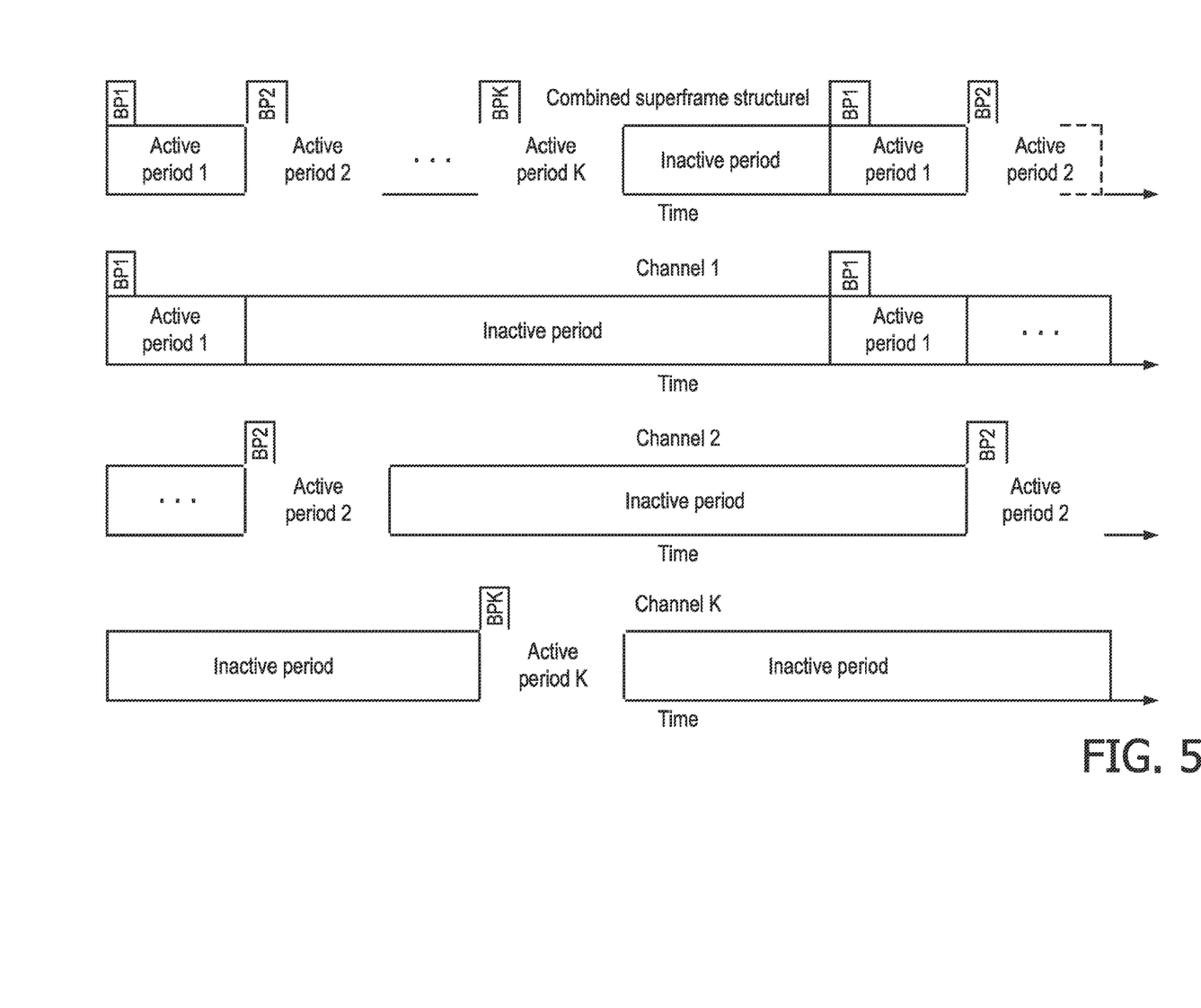
FIG. 5 illustrates maintenance of an MBAN according to a multi-channel communications scheme.

While the foregoing discussion was limited to two channels, it is to be understood that additional channels can be employed. In that regard, a channel in an MBAN band, typically including a duty cycle limit, is used as the primary channel and one or more channels in one or more other bands may be used as secondary channels. As above, the beacons of the primary channel include data allowing transmission to the secondary channels, and the active periods in the primary and secondary channels are non-overlapping to allow the hub device to operate in a manner similar to TDMA. FIG. 5 illustrates beacon based superframe structures of K>2 channels, as well as the combined superframe structure. The primary channel corresponds to channel 1, and the secondary channels corresponding to channels 2-K, in FIG. 5. Further, the beacons are abbreviated as "BP".

The multi-channel communication scheme is typically part of the media access control (MAC) and application level protocols of MBAN radios. It is compliant with the IEEE 802.15.4 and 802.15.6 protocols and can be implemented as firmware or software of the MBAN radios. Further, the multi-channel communication scheme can be used for MBAN based patient monitoring systems in which MBANs may work in a dedicated MBAN band, the 2.4 GHz ISM band, and/or even other RF bands. It can be also used for other wireless applications (e.g., wireless implanted devices) that need to operate in a dedicated band with duty cycle limits.

Figure 6:
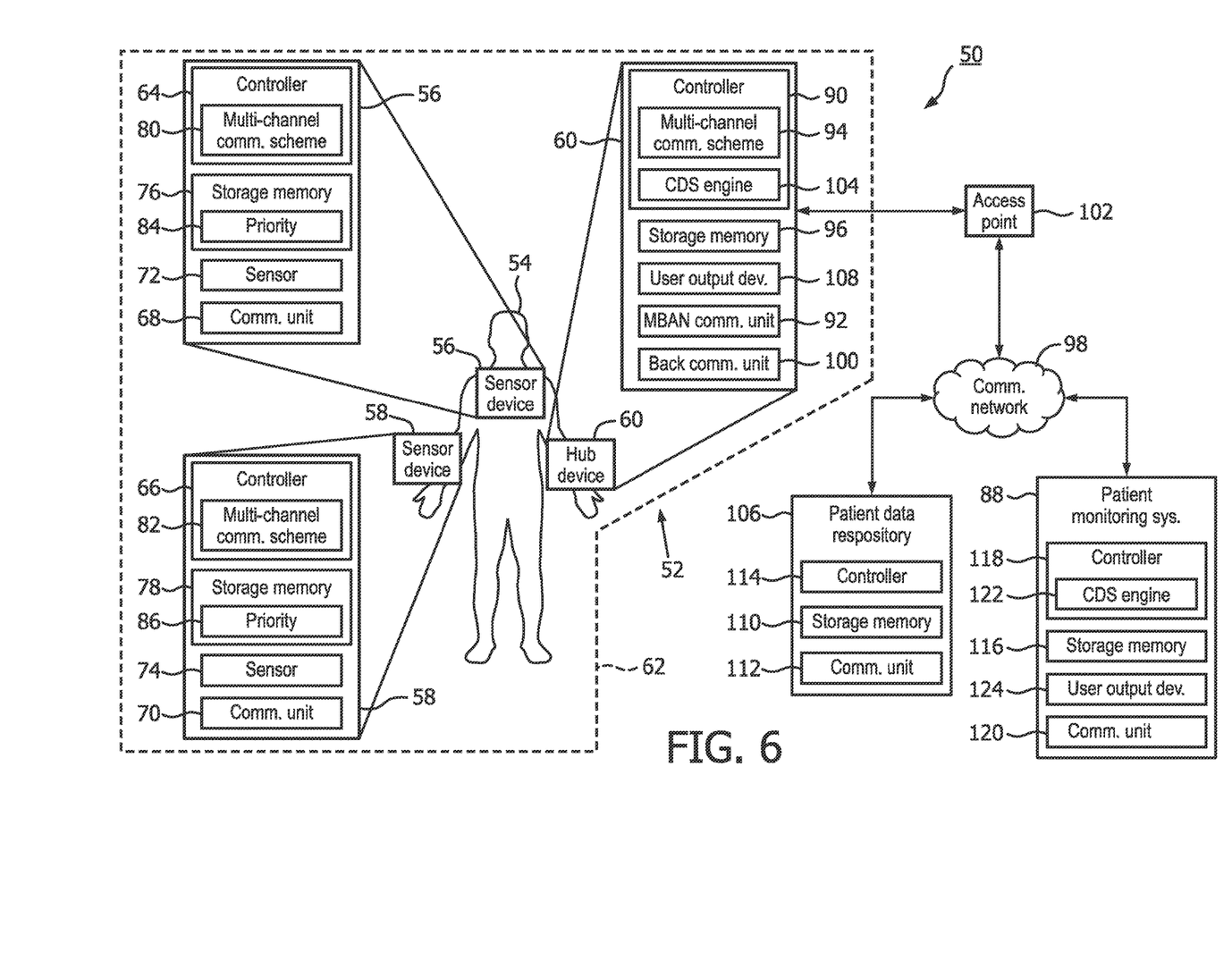
FIG. 6 illustrates a medical institution equipped with a multi-channel communications scheme.

With reference to FIG. 6, a medical institution 50 includes one or more MBAN systems 52 implementing the multi-channel communication scheme. The MBAN systems 52 are each associated with a patient 54 and are each deployed to capture physiological data of the patient 54. Further, each of the MBAN systems 52 includes one or more sensor devices 56, 58 and a hub device 60 acting as a coordinator device communicating over an MBAN 62 of the MBAN system 52.

The MBAN 62 is a low-power, short-range wireless network operating in a dedicated MBAN band, such as the 2360 megahertz (MHz) to 2400 MHz band in the U.S. and the 2483.5 MHz to 2500 MHz band proposed in Europe. The MBAN band includes a duty cycle limit, such as the 10% duty cycle limit proposed in Europe. The MBAN 62 further operates in one or more other bands, such as the 2.4 GHz ISM band, when approaching the duty cycle limit of the MBAN band. The MBAN band and the other bands are partitioned into channels managed by the hub device 60. The MBAN 62 is of any type, but typically one of an Institute of Electrical and Electronics Engineers (IEEE) 802.15.6 MBAN and an IEEE 802.15.4j MBAN.

The sensor devices 56, 68 capture physiological data of the patient 54, such as heart rate, respiration rate, blood pressure, electriocardiogram (ECG) signals, and so forth, in real-time and forward the data to the hub device 60 over the MBAN 62. The sensor devices 56, 58 are typically disposed on the exterior of the patient 54. For example, the sensor devices 56, 58 can be on-body and/or wearable sensor devices. However, in some embodiments, the sensor devices 56, 58 are additionally or alternatively disposed in the patient 54 and/or proximate to the patient 54.

Each of the sensor devices 56, 58 includes a controller 64, 66, a communication unit 68, 70, and at least one sensor 72, 74 for measuring at least one physiological parameter of the patient 54. The controller 64, 66 captures the physiological data using the sensor 72, 74 and transmits the captured physiological data to the hub device 60 using the communication unit 68, 70. The controller 64, 66 typically transmits the captured physiological data upon receiving it. However, in some embodiments, the controller 64, 66 buffers or otherwise stores the captured physiological data in at least one storage memory 76, 78 of the sensor device 56, 58 and transmits the buffered physiological data only when the amount exceeds a threshold. The controller 64, 66 further implements the multi-channel communications scheme by an included module 80, 82. The module 80, 82 is typically a software module stored on a program memory of the controller 64, 66 and executed by a processor of the controller 64, 66. The communication unit 68, 70 communicates with the hub device 60 over the MBAN 62 using the channels managed by the hub device 60. The channels are managed based on corresponding priority levels 84, 86 of the sensor devices 56, 58 stored in corresponding storage memories 76, 78.

Typically, the captured physiological data is transmitted directly to the hub device 60 using the communication unit 68, 70. However, in some embodiments, the captured physiological data is indirectly transmitted to the hub device 60. For example, the sensor devices 56, 58 can transmit the physiological data to a patient-carried unit with, for example, body coupled communications. The patient-carried unit can then transmit the physiological data from all of the sensor devices 56, 58 to the hub device 60.

The hub device 60 one or more of: 1) collects physiological data from the sensor devices 56, 58; 2) manages the sensor devices 56, 58 (e.g., acts as a personal area network (PAN) coordinator) and the channels in accordance with the multi-channel communications scheme; 3) processes collected physiological data locally, typically in real-time; and 4) transfers collected physiological data to a patient monitoring system 88 of the medical institution 50. The hub device 60 is typically disposed proximate to the patient 54. Further, the hub device 60 is typically one of a local bedside monitoring unit, a cell phone, a set-top-box, or other wireless device.

A controller 90 of the hub device 60 controls an MBAN communication unit 92 of the hub device 60 to set up the MBAN 62, associate/disassociate the sensor device 56, 58 and other devices with the MBAN 62, manage the channels of the MBAN band and the other band, and so on. The controller 90 carries out the foregoing in accordance with the multi-channel communications scheme by an included module 94. The module 80, 82 is typically a software module stored on a program memory of the controller 64, 66 and executed by a processor of the controller 64, 66. Further, the controller 90 collects the captured physiological data from the sensor devices 56, 58 using the MBAN communication unit 92. The MBAN communication unit 92 communicates with the sensor devices 56, 58 using the MBAN 62 and provides the controller 90 with an interface to the MBAN 62.

In some embodiments, physiological data collected by the controller 90 is transferred to the patient monitoring system 88 by the controller 90. Typically, the controller 90 immediately transfers the collected physiological data to the patient monitoring system 88 upon receiving it. Alternatively, in some embodiments, the controller 90 buffers or otherwise stores the collected physiological data in a storage memory 96 of the hub device 60 and transfers the buffered physiological data only when the amount exceeds a threshold.

The controller 90 transfers the collected physiological data to the patient monitoring system 88 over a communication network 98, such as a wired Ethernet, Wi-Fi, or third generation (3G) or fourth generation (4G) cellular network, using a backhaul communication unit 100. The backhaul communication network 98 is typically long-range compared to the MBAN 62. When the backhaul communication network 98 includes a wireless interface, it includes one or more backhaul access points 102 for wireless communication. The backhaul communication unit 100 communicates with the patient monitoring system 88 using the backhaul communication network 98 and provides the controller 90 with an interface to the backhaul communication network 98.

In some embodiments, the controller 90 locally processes the collected physiological data using a clinic decision support (CDS) engine 104. The CDS engine 104 is typically software executed by a processor of the controller 90. The CDS engine 104 provides a patient-centric personalized monitoring service based on the collected physiological data. In some embodiments, the CDS engine 104 also provides the patient-centric personalized monitoring service based on other patient related medical data (e.g., an electronic medical record (EMR), a lab report, etc.) available in one or more patient data repositories 106 of the backhaul communication network 98. The CDS engine 104 uses patient data (i.e., the collected physiological data and/or the other patient related medical data) to evaluate and predict patient condition, and/or to generate intelligent alarms as necessary.

In response to detecting an alarm condition, the CDS engine 104 generates warning messages, such as audio and/or visual warning messages using, for example, a user output device 108 (e.g., a display device) of the hub device 60. Additionally, or alternatively, the CDS engine 104 transmits an alarm message to a remote system or device, such as the patient monitoring system 88, using the MBAN or backhaul communication unit 92, 100 so as to allow the remote system or device to process the alarm and/or alert clinicians.

The patient data repositories 106 store patient medical patient data for the patients 54 of the medical institution 50 in one or more storage memories 110 of the patient data repositories 106. Examples of patient data include electronic medical records (EMRs), medical history data, lab reports, physiological data, and other relevant patient data. In some embodiments, the patient data repository 106 also stores other medical data useful for the clinical decision support algorithms of CDS engines, such as the CDS engine 104, in the storage memories 110. Examples of such other medical data include medical knowledge, demographic and/or geographic medical data, and so on.

Each of the patient data repositories 106 includes a communication unit 112 and a controller 114. The communication unit 112 allows the controller 114 to communicate with the backhaul communication network 98, and the controller 114 makes the data in the storage memories 110 available to external devices and/or systems over the backhaul communication network 98.

The patient monitoring system 88 one or more of: 1) receives physiological data transferred thereto by the hub devices 60 of the MBAN systems 52 over the backhaul communication network 98; 2) analyzes the received physiological data; 3) stores the received physiological data in a storage memory 116 of the patient monitoring system 88 or in an external system; and 4) provides one or more of monitoring, diagnosing and treating services in real time based on the received physiological data. The patient monitoring system 88 typically has access to the patient data repositories 106 to facilitate performance of the foregoing tasks. Further, the patient monitoring system 88 is remote from the MBAN systems 52 and typically central to the MBAN systems 52.

A controller 118 of the patient monitoring system 80 controls a communication unit 120 of the patient monitoring system 88 to receive physiological data from the MBAN systems 52. The communication unit 120 communicates with the backhaul communication network 98 and provides the controller 118 with an interface to the backhaul communication network 98. The received physiological data is typically stored in the storage memory 116 of the patient monitoring system 88.

In some embodiments, the controller 118 locally processes the received physiological data using a CDS engine 122. The CDS engine 122 is typically software executed by a processor of the controller 118. The CDS engine 122 provides a patient-centric personalized monitoring service based on the collected physiological data. In some embodiments, the CDS engine 122 also provides the patient-centric personalized monitoring service based on other patient related medical data (e.g., an EMR, a lab report, etc.) available in the patient data repositories 106. The CDS engine 122 uses patient data (i.e., the collected physiological data and/or the other patient related medical data) to evaluate and predict patient condition, and/or to generate intelligent alarms as necessary, for all or a subset of patients for which physiological data is received.

In response to detecting an alarm condition, the CDS engine 122 generates warning messages, such as audio and/or visual warning messages using, for example, a user output device 124 (e.g., a display device) of the patient monitoring system 88. Additionally, or alternatively, the CDS engine 122 transmits an alarm message to a remote system or device using the communication unit 120 so as to allow the remote system or device to process the alarm and/or alert clinicians.

For simplicity, only a single patient monitoring system 88 was described. However, in some embodiments, multiple patient monitoring systems are employed. In such embodiments, the MBAN systems 52 of the medical institution 50 are assigned to the available patient monitoring systems using any scheme designed to distribute the MBAN systems 52 across the patient monitoring systems. For example, each of the patient monitoring systems can be assigned a service zone of the medical institution 50, and each of the MBAN systems 52 can be assigned to the patient monitoring system corresponding to the service zone within which the MBAN system 52.

Figure 7:
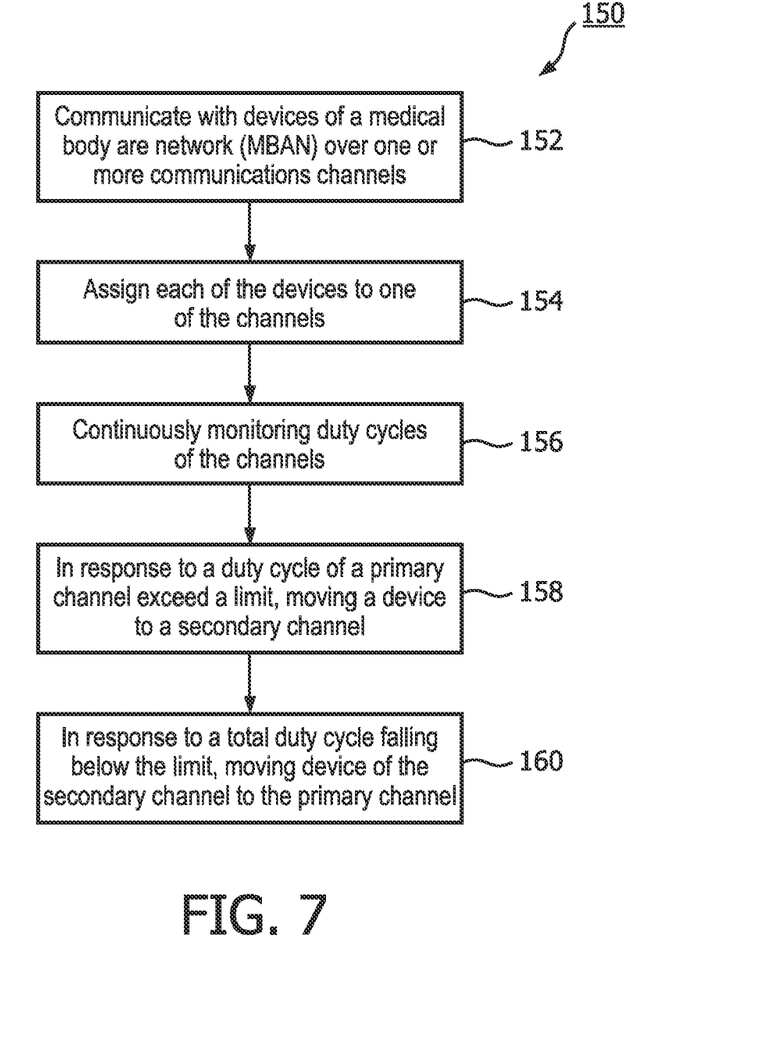
FIG. 7 illustrates a method for maintaining a MBAN in accordance with a multi-channel communications scheme.

With reference to FIG. 7, a method 150 for maintaining a MBAN 62 is provided. The MBAN 62 includes a hub or coordinator device 60 managing devices 56, 58, typically sensor devices, of the MBAN 62 by performing the method 150. According to the method 150, the hub or coordinator device 60 communicates 152 with the managed devices 56, 58 over one or more communication channels. The one or more communication channels include a primary channel with a duty cycle limit, typically in a dedicated MBAN band, and may include one or more secondary channels, typically in the ISM band.

Each of the managed devices 56, 58 is assigned 154 to one of the one or more channels based on priority level. In that regard, the managed devices 56, 58 each include pre-assigned priority levels, and the primary channel includes a minimum allowed priority level managed by the hub or coordinator device 60 based on the duty cycle of the primary channel. Where the minimum allowed priority level is zero, the managed devices 56, 58 are all assigned to the primary channel. Where the minimum allowed priority level is non-zero, high priority devices are assigned to the primary channel, and low priority devices are assigned to the one or more secondary channels. Managed devices 56, 58 with corresponding priority levels below the minimum allowed threshold level are low priority devices, and managed devices 56, 58 with corresponding priority levels above the minimum allowed threshold level are high priority devices. High priority devices can communicate on the secondary channels, whereas low priority devices can only communicate on the secondary channels.

The duty cycles of all channels upon which the hub or coordinator device 60 operates are continuously monitored 156. In response to the duty cycle of the primary channel exceeding the duty cycle limit, some of the devices assigned to the primary channel are moved 158 to a secondary channel. Where the hub or coordinator device 60 doesn't operate on a secondary channel, operation on a secondary channel is first initiated. In response to a total duty cycle of the one or more channels falling below the duty cycle limit, all devices 56, 58 assigned to secondary channels are moved 160 to the primary channel. Further, operation on the secondary channels ceases.

As used herein, a memory includes one or more of a non-transient computer readable medium; a magnetic disk or other magnetic storage medium; an optical disk or other optical storage medium; a random access memory (RAM), read-only memory (ROM), or other electronic memory device or chip or set of operatively interconnected chips; an Internet/Intranet server from which the stored instructions may be retrieved via the Internet/Intranet or a local area network; or so forth. Further, as used herein, a processor includes one or more of a microprocessor, a microcontroller, a graphic processing unit (GPU), an application-specific integrated circuit (ASIC), a field-programmable gate array (FPGA), and the like; a controller includes at least one memory and at least one processor, the processor executing processor executable instructions on the memory, or includes specialized hardware implementing a method; a communication unit includes a transceiver; a user input device includes one or more of a mouse, a keyboard, a touch screen display, one or more buttons, one or more switches, one or more toggles, and the like; and a display device includes one or more of a LCD display, an LED display, a plasma display, a projection display, a touch screen display, and the like.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A system for maintaining a medical body area network (MBAN), said system comprising:
    at least one controller configured to:
        communicate with devices of the MBAN over one or more channels of the MBAN, the one or more channels including a primary channel that includes a minimum allowed priority level, and each of the devices assigned to one of the one or more channels, wherein each of the devices includes a priority;
        continuously monitor a duty cycle of each of the one or more channels; and
        in response to the duty cycle of the primary channel meeting or exceeding a duty cycle limit, move a device of the devices to a secondary channel of the one or more channels based on the priority level of the device relative to the minimum allowed priority level;
    wherein the at least one controller is further configured to communicate with the devices over each of the primary and secondary channels using a beacon-based superframe structure;
    wherein periods of active transmission on the primary and secondary channels are non-overlapping;
    wherein beacons of the primary channel include data regarding the superframe structure of the secondary channel.

2. The system according to claim 1, wherein the controller is further configured to:
    in response to the duty cycle of the primary channel meeting or exceeding the duty cycle limit, initiate operation on the secondary channel.

3. The system according to claim 1, wherein the at least one controller is further configured to:
    in response to a total duty cycle of the one or more channels falling below the duty cycle limit and the one or more channels including the secondary channel, move all devices assigned to the secondary channel of the one or more channels to the primary channel.

4. The system according to claim 3, wherein the at least one controller is further configured to:
    in response to the total duty cycle of the one or more channels falling below the duty cycle limit and the one or more channels including the secondary channel, cease operation on the secondary channel.

5. The system according to claim 1, wherein the superframe structures of the primary and secondary channels share a common network identifier (ID) and device short addresses.

6. The system according to claim 1, wherein the primary channel includes a channel allocated for MBAN use with a duty cycle limit, and wherein the secondary channel includes a channel allocated for general use.

7. A method for maintaining a medical body area network (MBAN), said method comprising:
    communicating with devices of the MBAN over one or more channels of the MBAN, the one or more channels including a primary channel that includes a minimum allowed priority level and secondary channel, and each of the devices assigned to one of the one or more channels, wherein each of the devices includes a priority level;
    continuously monitoring a duty cycle of each of the one or more channels; and
    in response to the duty cycle of the primary channel meeting or exceeding a duty cycle limit, moving a device of the devices to a secondary channel based on the priority level of the device relative to the minimum allowed priority level;
    wherein the communicating with the devices over each of the primary and secondary channels uses a beacon-based superframe structure;
    wherein periods of active transmission on the primary and secondary channels are non-overlapping;
    wherein beacons of the primary channel include data regarding the superframe structure of the secondary channel.

8. The method according to claim 7, further including:
    in response to a total duty cycle of the one or more channels falling below the duty cycle limit and the one or more channels including the secondary channel, moving all devices assigned to the secondary channel of the one or more channels to the primary channel.

9. The method according to claim 8, further including:
    in response to the total duty cycle of the one or more channels falling below the duty cycle limit and the one or more channels including the secondary channel, ceasing operation on the secondary channel.

10. The method according to claim 7, wherein the primary channel includes a channel allocated for MBAN use with a duty cycle limit, and wherein the secondary channel includes a channel allocated for general use.

11. At least one controller configured to perform the method according to claim 7.

12. The method according to claim 7, further including, continuously monitoring a duty cycle of each of the one or more channels; and
    in response to the duty cycle of the primary channel exceeding a duty cycle limit, moving a device of the devices to the secondary channel.

* * * * *